United States Patent
Degering et al.

(10) Patent No.: US 12,157,870 B2
(45) Date of Patent: Dec. 3, 2024

(54) AGENT CONTAINING A RECOMBINANT POLYESTERASE

(71) Applicant: Henkel AG & Co. KGaA, Duesseldorf (DE)

(72) Inventors: Christian Degering, Erkrath (DE); Jasmin Eidner, Wiesbaden (DE); Thomas Haarmann, Zwingenberg (DE); Shohana Islam, Rheinbach (DE); Felix Jakob, Erkelenz (DE); Patrick Lorenz, Lorsch (DE); Nina Mussmann, Willich (DE); Kristin Ruebsam, Aachen (DE); Ulrich Schwaneberg, Kelmis-Hergenrath (BE); Ruth Schwerdtfeger, Darmstadt (DE); Lina Apitius, Dreieich (DE); Ren Wei, Borsdorf (DE); Susanne Wieland, Zons/Dormagen (DE); Wolfgang Zimmermann, Leipzig (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 761 days.

(21) Appl. No.: 16/973,482

(22) PCT Filed: Jun. 25, 2019

(86) PCT No.: PCT/EP2019/066793
§ 371 (c)(1),
(2) Date: Dec. 9, 2020

(87) PCT Pub. No.: WO2020/002308
PCT Pub. Date: Jan. 2, 2020

(65) Prior Publication Data
US 2021/0246400 A1    Aug. 12, 2021

(30) Foreign Application Priority Data
Jun. 28, 2018  (DE) ..................... 10 2018 210 605.3

(51) Int. Cl.
*C11D 3/386*    (2006.01)
*C12N 9/18*    (2006.01)

(52) U.S. Cl.
CPC ............ *C11D 3/38636* (2013.01); *C12N 9/18* (2013.01); *C11D 2111/12* (2024.01)

(58) Field of Classification Search
None
See application file for complete search history.

(56) References Cited

U.S. PATENT DOCUMENTS

| | | | |
|---|---|---|---|
| 6,313,081 | B1 | 11/2001 | Lenting et al. |
| 2014/0073029 | A1 | 3/2014 | DiCosimo et al. |
| 2021/0254036 | A1 | 8/2021 | Degering et al. |

FOREIGN PATENT DOCUMENTS

| | | |
|---|---|---|
| DE | 69632910 T3 | 9/2009 |
| WO | 2010069742 A1 | 6/2010 |
| WO | 2012113827 A1 | 8/2012 |
| WO | 2013033318 A1 | 3/2013 |
| WO | 2013096653 A1 | 6/2013 |
| WO | 2016206838 A1 | 12/2016 |
| WO | 2017129436 A1 | 8/2017 |

OTHER PUBLICATIONS

Ribitsch et al. "Enhanced Cutinase-Catalyzed Hydrolysis of Polyethylene Terephthalate by Covalent Fusion to Hydrophobins" Applied and Environmental Microbiology 81:3586-3592. (Year: 2015).*
Anonymous "A0A7D5LZ99 A0A7D5LZ99_HYPJE" https://www.uniprot.org/uniprotkb/A0A7D5LZ99/entry (Year: 2020).*
Anonymous "A0A1P8YYE3 A0A1P8YYE3_HYPVI" https://www.uniprot.org/uniprotkb/A0A1P8YYE3/entry (Year: 2017).*
Anonymous "A0A2U9QZ1X0 A0A2U9Q1X0_TRIHA" https://www.uniprot.org/uniprotkb/A0A2U9Q1X0/entry (Year: 2018).*
Ribitsch et al.: "Enhanced Cutinase-Catalyzed Hydrolysis of Polyethylene Terephthalate by Covalent Fusion to Hydrophobins", Applied and Environmental Microbiology, Jun. 2015, vol. 81, No. 11, pp. 3586-3592.
Ribitsch et al.: "Fusion of Binding Domains to Thermobifida cellulosilytica Cutinase to Tune Sorption Characteristics and Enhancing PET Hydrolysis", Biomacromolecules 2013, vol. 14, pp. 1769-1776, American Chemical Society.
International search report from parallel PCT Patent Application PCT/EP2019/066793 dated Sep. 24, 2019, 5 pages.
Ruebsam et al.: "Anchor peptides: A green and versatile method for polypropylene functionalization", Polymer 116, (2017), pp. 124-132, Elsevier Ltd.
Wei, Ren et al.: "Functional characterization and structural modeling of synthetic polyester-degrading hydrolases from Thermomonospora curvata", AMB Express 2014, 4:44, Jun. 3, 2014, pp. 1-10, Springer.
NCBI Accession Nr. CDN67545.1 "Triacylglycerol lipase, partial [synthetic construct]", 2 pages.
Franceus; "Correlated positions in protein evolution and engineering"; Journal Ind Microbiol Biotechnol, vol. 44, Issue No. 4-5; pp. 687-695 (2017).
Leitao, A. et al.; "Structural Insights into Carboxylic Polyester-Degrading Enzymes and Their Functional Depolymerizing Neighbors"; International Journal of Molecular Sciences, vol. 22, Issue 2332; 14 pgs (2021) DOI: https://doi.org/10.3390/ijms22052332.
Sanavia; "Limitations and challenges in protein stability prediction upon genome variations: towards future applications in precision medicine"; Computational and Structural Biotechnology Journal, vol. 18; pp. 1968-1979 (2020).

(Continued)

*Primary Examiner* — Sudhakar Katakam
*Assistant Examiner* — Zachary J Miknis
(74) *Attorney, Agent, or Firm* — CANTOR COLBURN LLP

(57) ABSTRACT

An agent, such as a detergent or cleaning agent, may include a polyesterase. A method for cleaning textiles may include applying the agent to a textile for removing soiling. The polyesterase may also help to reduce pilling effects in the agent.

19 Claims, No Drawings
Specification includes a Sequence Listing.

(56) References Cited

OTHER PUBLICATIONS

Wei, R. et al.; "Functional characterization and structural modeling of synthetic polyester-degrading hydrolases from Thermomonospora curvata"; AMB Express, vol. 4; 10 pages (2014) DOI:http://amb-express.com/content/4/1/44.
Anon, "NCBI Reference Sequence: WP_012850775.1"; 1 page.
Anon, UniProtKB/TrEMPL, D1A2H1_THECD (2017).
International Search Report for International Application PCT/EP2019/066795; International Filing Date: Sep. 24, 2019; 4 pages.
Studer; "Residue mutations and their impact on protein structure and function: detecting beneficial and pathogenic changes"; Biochem Journal, vol. 493; pp. 581-594 (2013).
Written Opinion for International Application PCT/EP2019/066793; International Filing Date: Jun. 25, 2019; Date of Mailing: Sep. 24, 2019; 4 pages.
Written Opinion for International Application PCT/EP2019/066795; International Filing Date: Jun. 25, 2019; Date of Mailing: Sep. 24, 2019; 4 pages.

\* cited by examiner

SEQUENCE LISTING

```
<160> NUMBER OF SEQ ID NOS: 12

<210> SEQ ID NO 1
<211> LENGTH: 261
<212> TYPE: PRT
<213> ORGANISM: Thermomonospora curvata DSM 43183

<400> SEQUENCE: 1

Ala Ala Asn Pro Tyr Gln Arg Gly Pro Asp Pro Thr Glu Ser Leu Leu
1               5                   10                  15

Arg Ala Ala Arg Gly Pro Phe Ala Val Ser Glu Gln Ser Val Ser Arg
            20                  25                  30

Leu Ser Val Ser Gly Phe Gly Gly Arg Ile Tyr Tyr Pro Thr Thr
        35                  40                  45

Thr Ser Gln Gly Thr Phe Gly Ala Ile Ala Ile Ser Pro Gly Phe Thr
    50                  55                  60

Ala Ser Trp Ser Ser Leu Ala Trp Leu Gly Pro Arg Leu Ala Ser His
65                  70                  75                  80

Gly Phe Val Val Ile Gly Ile Glu Thr Asn Thr Arg Leu Asp Gln Pro
                85                  90                  95

Asp Ser Arg Gly Arg Gln Leu Leu Ala Ala Leu Asp Tyr Leu Thr Gln
            100                 105                 110

Arg Ser Ser Val Arg Asn Arg Val Asp Ala Ser Arg Leu Ala Val Ala
        115                 120                 125

Gly His Ser Met Gly Gly Gly Thr Leu Glu Ala Ala Lys Ser Arg
    130                 135                 140

Thr Ser Leu Lys Ala Ala Ile Pro Ile Ala Pro Trp Asn Leu Asp Lys
145                 150                 155                 160
```

```
Thr Trp Pro Glu Val Arg Thr Pro Thr Leu Ile Ile Gly Gly Glu Leu
                165                 170                 175

Asp Ser Ile Ala Pro Val Ala Thr His Ser Ile Pro Phe Tyr Asn Ser
            180                 185                 190

Leu Thr Asn Ala Arg Glu Lys Ala Tyr Leu Glu Leu Asn Asn Ala Ser
        195                 200                 205

His Phe Phe Pro Gln Phe Ser Asn Asp Thr Met Ala Lys Phe Met Ile
    210                 215                 220

Ser Trp Met Lys Arg Phe Ile Asp Asp Thr Arg Tyr Asp Gln Phe
225                 230                 235                 240

Leu Cys Pro Pro Arg Ala Ile Gly Asp Ile Ser Asp Tyr Arg Asp
                245                 250                 255

Thr Cys Pro His Thr
            260

<210> SEQ ID NO 2
<211> LENGTH: 44
<212> TYPE: PRT
<213> ORGANISM: Tachypleus tridentatus

<400> SEQUENCE: 2

Tyr Ser Arg Cys Gln Leu Gln Gly Phe Asn Cys Val Val Arg Ser Tyr
1               5                   10                  15

Gly Leu Pro Thr Ile Pro Cys Cys Arg Gly Leu Thr Cys Arg Ser Tyr
            20                  25                  30

Phe Pro Gly Ser Thr Tyr Gly Arg Cys Gln Arg Tyr
            35                  40

<210> SEQ ID NO 3
<211> LENGTH: 25
<212> TYPE: PRT
<213> ORGANISM: Androctonus australis

<400> SEQUENCE: 3

Arg Ser Val Cys Arg Gln Ile Lys Ile Cys Arg Arg Gly Gly Cys
1               5                   10                  15

Tyr Tyr Lys Cys Thr Asn Arg Pro Tyr
            20                  25

<210> SEQ ID NO 4
<211> LENGTH: 47
<212> TYPE: PRT
<213> ORGANISM: Bacillus subtilis

<400> SEQUENCE: 4

Ala Ile Lys Leu Val Gln Ser Pro Asn Gly Asn Phe Ala Ala Ser Phe
1               5                   10                  15

Val Leu Asp Gly Thr Lys Trp Ile Phe Lys Ser Lys Tyr Tyr Asp Ser
            20                  25                  30

Ser Lys Gly Tyr Trp Val Gly Ile Tyr Glu Val Trp Asp Arg Lys
            35                  40                  45

<210> SEQ ID NO 5
<211> LENGTH: 21
<212> TYPE: PRT
<213> ORGANISM: Podisus maculiventris

<400> SEQUENCE: 5

Gly Ser Lys Lys Pro Val Pro Ile Ile Tyr Cys Asn Arg Arg Thr Gly
1               5                   10                  15
```

```
Lys Cys Gln Arg Met
            20

<210> SEQ ID NO 6
<211> LENGTH: 17
<212> TYPE: PRT
<213> ORGANISM: Artificial
<220> FEATURE:
<223> OTHER INFORMATION: Peptide linker

<400> SEQUENCE: 6

Ala Glu Ala Ala Ala Lys Glu Ala Ala Ala Lys Glu Ala Ala Ala Lys
1               5                   10                  15

Ala

<210> SEQ ID NO 7
<211> LENGTH: 24
<212> TYPE: PRT
<213> ORGANISM: Artificial
<220> FEATURE:
<223> OTHER INFORMATION: Peptide linker

<400> SEQUENCE: 7

Pro Pro Gly Gly Asn Arg Gly Thr Thr Thr Thr Arg Arg Pro Ala Thr
1               5                   10                  15

Thr Thr Gly Ser Ser Pro Gly Pro
            20

<210> SEQ ID NO 8
<211> LENGTH: 321
<212> TYPE: PRT
<213> ORGANISM: Artificial
<220> FEATURE:
<223> OTHER INFORMATION: Polyesterase construct

<400> SEQUENCE: 8

Ala Ala Asn Pro Tyr Gln Arg Gly Pro Asp Pro Thr Glu Ser Leu Leu
1               5                   10                  15

Arg Ala Ala Arg Gly Pro Phe Ala Val Ser Glu Gln Ser Val Ser Arg
            20                  25                  30

Leu Ser Val Ser Gly Phe Gly Gly Gly Arg Ile Tyr Tyr Pro Thr Thr
        35                  40                  45

Thr Ser Gln Gly Thr Phe Gly Ala Ile Ala Ile Ser Pro Gly Phe Thr
    50                  55                  60

Ala Ser Trp Ser Ser Leu Ala Trp Leu Gly Pro Arg Leu Ala Ser His
65                  70                  75                  80

Gly Phe Val Val Ile Gly Ile Glu Thr Asn Thr Arg Leu Asp Gln Pro
                85                  90                  95

Asp Ser Arg Gly Arg Gln Leu Leu Ala Ala Leu Asp Tyr Leu Thr Arg
            100                 105                 110

Ser Ser Val Arg Asn Arg Val Asp Ala Ser Arg Leu Ala Val Ala Gly
        115                 120                 125

His Ser Met Gly Gly Gly Gly Thr Leu Glu Ala Ala Lys Ser Arg Thr
    130                 135                 140

Ser Leu Lys Ala Ala Ile Pro Ile Ala Pro Trp Asn Leu Asp Lys Thr
145                 150                 155                 160

Trp Pro Glu Val Arg Thr Pro Thr Leu Ile Ile Gly Gly Glu Leu Asp
                165                 170                 175

Ser Ile Ala Pro Val Ala Thr His Ser Ile Pro Phe Tyr Asn Ser Leu
```

```
                    180                 185                 190
Thr Asn Ala Arg Glu Lys Ala Tyr Leu Glu Leu Asn Asn Ala Ser His
            195                 200                 205
Phe Phe Pro Gln Phe Ser Asn Asp Thr Met Ala Lys Phe Met Ile Ser
        210                 215                 220
Trp Met Lys Arg Phe Ile Asp Asp Thr Arg Tyr Asp Gln Phe Leu
225                 230                 235                 240
Cys Pro Pro Arg Ala Ile Gly Asp Ile Ser Asp Tyr Arg Asp Thr
            245                 250                 255
Cys Pro His Thr Ala Glu Ala Ala Lys Glu Ala Ala Lys Glu
            260                 265                 270
Ala Ala Ala Lys Ala Tyr Ser Arg Cys Gln Leu Gln Gly Phe Asn Cys
            275                 280                 285
Val Val Arg Ser Tyr Gly Leu Pro Thr Ile Pro Cys Cys Arg Gly Leu
            290                 295                 300
Thr Cys Arg Ser Tyr Phe Pro Gly Ser Thr Tyr Gly Arg Cys Gln Arg
305                 310                 315                 320
Tyr

<210> SEQ ID NO 9
<211> LENGTH: 328
<212> TYPE: PRT
<213> ORGANISM: Artificial
<220> FEATURE:
<223> OTHER INFORMATION: Polyesterase construct

<400> SEQUENCE: 9

Ala Ala Asn Pro Tyr Gln Arg Gly Pro Asp Pro Thr Glu Ser Leu Leu
1               5                   10                  15
Arg Ala Ala Arg Gly Pro Phe Ala Val Ser Glu Gln Ser Val Ser Arg
            20                  25                  30
Leu Ser Val Ser Gly Phe Gly Gly Gly Arg Ile Tyr Tyr Pro Thr Thr
        35                  40                  45
Thr Ser Gln Gly Thr Phe Gly Ala Ile Ala Ile Ser Pro Gly Phe Thr
    50                  55                  60
Ala Ser Trp Ser Ser Leu Ala Trp Leu Gly Pro Arg Leu Ala Ser His
65                  70                  75                  80
Gly Phe Val Val Ile Gly Ile Glu Thr Asn Thr Arg Leu Asp Gln Pro
                85                  90                  95
Asp Ser Arg Gly Arg Gln Leu Leu Ala Ala Leu Asp Tyr Leu Thr Arg
            100                 105                 110
Ser Ser Val Arg Asn Arg Val Asp Ala Ser Arg Leu Ala Val Ala Gly
        115                 120                 125
His Ser Met Gly Gly Gly Gly Thr Leu Glu Ala Ala Lys Ser Arg Thr
    130                 135                 140
Ser Leu Lys Ala Ala Ile Pro Ile Ala Pro Trp Asn Leu Asp Lys Thr
145                 150                 155                 160
Trp Pro Glu Val Arg Thr Pro Thr Leu Ile Ile Gly Gly Glu Leu Asp
                165                 170                 175
Ser Ile Ala Pro Val Ala Thr His Ser Ile Pro Phe Tyr Asn Ser Leu
            180                 185                 190
Thr Asn Ala Arg Glu Lys Ala Tyr Leu Glu Leu Asn Asn Ala Ser His
        195                 200                 205
Phe Phe Pro Gln Phe Ser Asn Asp Thr Met Ala Lys Phe Met Ile Ser
    210                 215                 220
```

```
Trp Met Lys Arg Phe Ile Asp Asp Asp Thr Arg Tyr Asp Gln Phe Leu
225                 230                 235                 240

Cys Pro Pro Arg Ala Ile Gly Asp Ile Ser Asp Tyr Arg Asp Thr
            245                 250                 255

Cys Pro His Thr Pro Gly Gly Asn Arg Gly Thr Thr Thr Arg
        260                 265                 270

Arg Pro Ala Thr Thr Thr Gly Ser Ser Pro Gly Pro Tyr Ser Arg Cys
            275                 280                 285

Gln Leu Gln Gly Phe Asn Cys Val Val Arg Ser Tyr Gly Leu Pro Thr
            290                 295                 300

Ile Pro Cys Cys Arg Gly Leu Thr Cys Arg Ser Tyr Phe Pro Gly Ser
305                 310                 315                 320

Thr Tyr Gly Arg Cys Gln Arg Tyr
                325
```

<210> SEQ ID NO 10
<211> LENGTH: 289
<212> TYPE: PRT
<213> ORGANISM: Thermomonospora curvata DSM 43183

<400> SEQUENCE: 10

```
Met Ser Leu Arg Lys Ser Phe Gly Leu Leu Ser Ala Thr Ala Ala Leu
1               5                   10                  15

Val Ala Gly Leu Val Ala Ala Pro Ala Gln Ala Ala Asn Pro
            20                  25                  30

Tyr Gln Arg Gly Pro Asp Pro Thr Glu Ser Leu Leu Arg Ala Ala Arg
            35                  40                  45

Gly Pro Phe Ala Val Ser Glu Gln Ser Val Ser Arg Leu Ser Val Ser
50                  55                  60

Gly Phe Gly Gly Gly Arg Ile Tyr Tyr Pro Thr Thr Thr Ser Gln Gly
65                  70                  75                  80

Thr Phe Gly Ala Ile Ala Ile Ser Pro Gly Phe Thr Ala Ser Trp Ser
                85                  90                  95

Ser Leu Ala Trp Leu Gly Pro Arg Leu Ala Ser His Gly Phe Val Val
            100                 105                 110

Ile Gly Ile Glu Thr Asn Thr Arg Leu Asp Gln Pro Asp Ser Arg Gly
            115                 120                 125

Arg Gln Leu Leu Ala Ala Leu Asp Tyr Leu Thr Gln Arg Ser Ser Val
130                 135                 140

Arg Asn Arg Val Asp Ala Ser Arg Leu Ala Val Ala Gly His Ser Met
145                 150                 155                 160

Gly Gly Gly Gly Thr Leu Glu Ala Ala Lys Ser Arg Thr Ser Leu Lys
                165                 170                 175

Ala Ala Ile Pro Ile Ala Pro Trp Asn Leu Asp Lys Thr Trp Pro Glu
            180                 185                 190

Val Arg Thr Pro Thr Leu Ile Ile Gly Gly Glu Leu Asp Ser Ile Ala
            195                 200                 205

Pro Val Ala Thr His Ser Ile Pro Phe Tyr Asn Ser Leu Thr Asn Ala
210                 215                 220

Arg Glu Lys Ala Tyr Leu Glu Leu Asn Asn Ala Ser His Phe Phe Pro
225                 230                 235                 240

Gln Phe Ser Asn Asp Thr Met Ala Lys Phe Met Ile Ser Trp Met Lys
            245                 250                 255

Arg Phe Ile Asp Asp Asp Thr Arg Tyr Asp Gln Phe Leu Cys Pro Pro
```

```
                260                 265                 270
Pro Arg Ala Ile Gly Asp Ile Ser Asp Tyr Arg Asp Thr Cys Pro His
            275                 280                 285
Thr

<210> SEQ ID NO 11
<211> LENGTH: 261
<212> TYPE: PRT
<213> ORGANISM: Artificial
<220> FEATURE:
<223> OTHER INFORMATION: Hybrid Polyesterase

<400> SEQUENCE: 11

Ala Asn Pro Tyr Gln Arg Gly Pro Asn Pro Thr Arg Ser Ala Leu Thr
1               5                   10                  15

Ala Asp Gly Pro Phe Ser Val Ala Thr Tyr Thr Val Ser Arg Leu Ser
            20                  25                  30

Val Ser Gly Phe Gly Gly Gly Val Ile Tyr Tyr Pro Thr Gly Thr Ser
        35                  40                  45

Leu Thr Phe Gly Gly Ile Ala Met Ser Pro Gly Tyr Thr Ala Asp Ala
    50                  55                  60

Ser Ser Leu Ala Trp Leu Gly Arg Arg Leu Ala Ser His Gly Phe Val
65                  70                  75                  80

Val Leu Val Ile Asn Thr Asn Ser Arg Phe Asp Tyr Pro Asp Ser Arg
                85                  90                  95

Ala Ser Gln Leu Ser Ala Ala Leu Asn Tyr Leu Arg Thr Ser Ser Pro
            100                 105                 110

Ser Ala Val Arg Ala Arg Leu Asp Ala Asn Arg Leu Ala Val Ala Gly
        115                 120                 125

His Ser Met Gly Gly Gly Gly Thr Leu Arg Ile Ala Glu Gln Asn Pro
    130                 135                 140

Ser Leu Lys Ala Ala Ile Pro Leu Thr Pro Trp His Leu Asn Lys Asn
145                 150                 155                 160

Trp Ser Ser Val Thr Val Pro Thr Leu Ile Ile Gly Ala Asp Leu Asp
                165                 170                 175

Thr Ile Ala Pro Val Ser Gln His Ala Ile Pro Phe Tyr Gln Asn Leu
            180                 185                 190

Pro Ser Thr Thr Pro Lys Val Tyr Val Glu Leu Asp Asn Ala Ser His
        195                 200                 205

Phe Ala Pro Asn Ser Asn Asn Ala Ala Ile Ser Val Tyr Thr Ile Ser
    210                 215                 220

Trp Met Lys Leu Trp Val Asp Asn Asp Thr Arg Tyr Arg Gln Phe Leu
225                 230                 235                 240

Cys Asn Val Asn Asp Pro Ala Leu Ser Asp Phe Arg Thr Asn Asn Arg
                245                 250                 255

His Cys Gln Leu Glu
            260

<210> SEQ ID NO 12
<211> LENGTH: 262
<212> TYPE: PRT
<213> ORGANISM: Thermomonospora curvata

<400> SEQUENCE: 12

Ala Ala Asn Pro Tyr Gln Arg Gly Pro Asn Pro Thr Glu Ala Ser Ile
1               5                   10                  15
```

-continued

```
Thr Ala Ala Arg Gly Pro Phe Asn Thr Ala Glu Ile Thr Val Ser Arg
            20              25              30

Leu Ser Val Ser Gly Phe Gly Gly Lys Ile Tyr Tyr Pro Thr Thr
        35              40              45

Thr Ser Glu Gly Thr Phe Gly Ala Ile Ala Ile Ser Pro Gly Phe Thr
    50              55              60

Ala Tyr Trp Ser Ser Leu Glu Trp Leu Gly His Arg Leu Ala Ser Gln
65              70              75              80

Gly Phe Val Val Ile Gly Ile Glu Thr Asn Thr Thr Leu Asp Gln Pro
                85              90              95

Asp Gln Arg Gly Gln Gln Leu Leu Ala Ala Leu Asp Tyr Leu Thr Gln
            100             105             110

Arg Ser Ala Val Arg Asp Arg Val Asp Ala Ser Arg Leu Ala Val Ala
        115             120             125

Gly His Ser Met Gly Gly Gly Gly Ser Leu Glu Ala Ala Lys Ala Arg
    130             135             140

Thr Ser Leu Lys Ala Ala Ile Pro Leu Ala Pro Trp Asn Leu Asp Lys
145             150             155             160

Thr Trp Pro Glu Val Arg Thr Pro Thr Leu Ile Ile Gly Gly Glu Leu
                165             170             175

Asp Ala Val Ala Pro Val Ala Thr His Ser Ile Pro Phe Tyr Asn Ser
            180             185             190

Leu Ser Asn Ala Pro Glu Lys Ala Tyr Leu Glu Leu Asp Asn Ala Ser
        195             200             205

His Phe Phe Pro Asn Ile Thr Asn Thr Gln Met Ala Lys Tyr Met Ile
    210             215             220

Ala Trp Met Lys Arg Phe Ile Asp Asp Asp Thr Arg Tyr Thr Gln Phe
225             230             235             240

Leu Cys Pro Pro Pro Ser Thr Gly Leu Leu Ser Asp Phe Ser Asp Ala
                245             250             255

Arg Phe Thr Cys Pro Met
            260
```

AGENT CONTAINING A RECOMBINANT POLYESTERASE

REFERENCE TO A SEQUENCE LISTING SUBMITTED VIA EFS-WEB

The content of the ASCII text file of the sequence listing named "2018PF35185-Sequence_protocol", which is 18 kb in size was created on Jun. 28, 2018 and electronically submitted via EFS-Web herewith the application is incorporated by reference in its entirety.

CROSS-REFERENCE TO RELATED APPLICATIONS

The present application is a national stage entry according to 35 U.S.C. § 371 of PCT application No.: PCT/EP2019/066793 filed on Jun. 25, 2019; which claims priority to German Patent Application Serial No.: 10 2018 210 605.3 filed on Jun. 28, 2018; all of which are incorporated herein by reference in their entirety and for all purposes.

TECHNICAL FIELD

The present invention is in the field of enzyme technology, in particular the anti-pilling effect of enzymes, such as those used in washing or cleaning agents. The invention relates to agents, in particular washing or cleaning agents, which contain a polyesterase as defined herein. The present invention further relates to a method for cleaning textiles and to the use of the agent according to the invention for removing stains. Furthermore, the invention is directed to the use of a polyesterase, as described herein, for reducing pilling effects and preventing graying in an agent, such as a washing or cleaning agent.

BACKGROUND

If washed several times, all types of textiles will pill over time. Pilling refers to the formation of nodules or lint in fabrics. These small pieces of lint are particularly common with short-fiber fabrics. With long-fiber and twisted fibers, however, there is less pilling. Generally, these nodules are caused by loose fibers in the fabric or those that have come loose from the fabric. Due to their smooth surface, synthetic fibers are prone to pilling more than natural fibers, because synthetic fibers can be released from the fabric faster than rough natural fibers. In the case of wool fabrics, these fibers "mat" mainly due to mechanical friction and form nodules on the surface.

The main impact of pilling is an adverse visual effect. Due to the formation of nodules on the surface, fabrics quickly look used and older than they are. In addition, colored textiles appear less brilliant. In contrast, the functionality of the fabric is hardly or not at all impaired. Pilling takes place in particular at places that are subject to high mechanical stress, usually in the shoulder and waist region. Due to the continuous thinning of the fabric, these stressed regions are particularly at risk of forming holes or even tearing. The undesirable pilling has the consequence that correspondingly impaired textiles are rejected and thrown away by consumers more quickly than would be necessary on the basis of the functionality of the textile.

Furthermore, textiles tend to turn gray when washed. This is because both dirt and detached pigments are released from colored clothes in the washing process. Although attempts are made to keep said dirt and pigments in the washing liquor by means of various washing agent ingredients, it is often not possible to prevent the dirt/pigments from being deposited on the clothing and remaining there. This is the so-called graying effect. This is particularly pronounced for some synthetic fibers such as polyamide, but also polyester.

A technical solution to reduce the pilling effect has so far only been available for cotton textiles. Cellulases are used in the cleaning agent to reduce the pilling effect (DE 69632910 T3). This means that cellulases are used in the washing agent to have anti-pilling or anti-graying effects and thus ensure that clothes look like new for longer. However, cellulases only work on cotton textiles. For other textiles, such as polyester textiles, there is no comparable way to reduce pilling. Therefore, it is desirable and there is a demand for solutions that reduce the pilling of textiles, in particular textiles that contain synthetic fibers such as polyester, in order to keep clothes looking new for as long as possible, i.e. the colors should remain strong, the shape should be preserved and the surfaces should remain smooth and undamaged.

SUMMARY

Surprisingly, the inventors have found that the performance of polyesterases can be significantly increased if they are fused with special peptide anchor molecules which have a binding affinity for polyester. This effect has been demonstrated herein using an example polyesterase, but it can also be transferred to other enzymes. The polyesterase used and described herein from *Thermomonospora curvata* DSM 43183 is active under washing process conditions and has various nourishing properties for PET textiles. The polyesterase used demonstrates rapid PET degradation at 40° ° C. The enzyme prevents pilling on new polyester textiles or facilitates this effect in combination with a cellulase on polyester/cotton blended textiles. In addition, pills that have already been formed can be reduced, i.e. it can produce what is referred to as a "renew" effect. The polyesterase also prevents the graying of white laundry and the fading/graying of colored laundry. With the appropriate dosage, all of these positive washing properties are achieved without significantly damaging the fiber. The performance of enzymes of this kind can be increased by fusion with a peptide which has an affinity for polyester fibers in such a way that the concentration used can be significantly reduced without loss of performance.

Therefore, in a first aspect, the agent, in particular a washing or cleaning agent, is characterized in that it contains a polyesterase which is covalently bonded to at least one heterologous peptide sequence which has an affinity for polyesters. The peptide sequence which has an affinity for polyesters is not naturally linked to the polyesterase, i.e. is heterologous relative to the polyesterase sequence. The enzymes described herein are therefore not naturally occurring enzymes, but fusion proteins comprising a polyesterase and a peptide sequence which has an affinity for polyesters.

In a further aspect, the methods for cleaning textiles, is characterized in that an agent is used in at least one method step. The textiles are polyester-containing textiles or consist of polyester.

In another aspect, the use of an agent as described herein, such as a washing or cleaning agent, such as a liquid washing agent, for removing stains.

In addition, a further aspect includes the use of the polyesterase described herein for reducing pilling effects and/or increasing the anti-graying effect of an agent, such as a washing or cleaning agent, or a liquid washing agent, the agent containing the polyesterase.

DETAILED DESCRIPTION

"At least one," as used herein, means one or more, for example 1, 2, 3, 4, 5, 6, 7, 8, 9 or more. In relation to a constituent or a compound, unless stated otherwise, this expression does not refer to the absolute number of molecules, but rather to the number of different types of molecules that fall under the relevant definition of the constituent or compound. "At least one polyesterase" thus means that at least one type of polyesterase is contained, and not that at least one polyesterase molecule is contained.

"Heterologous," as used herein with reference to the peptide sequence, refers to the fact that the peptide sequence which has an affinity for polyesters does not naturally occur in combination with the polyesterase. The enzymes described herein are thus non-natural hybrids of a polyesterase and a peptide not associated with the polyesterase.

"Affinity for polyester," as used herein, means that the corresponding peptide sequence binds to polyester, in particular polyester fibers, such as those used in textiles, under suitable conditions, i.e. usually non-denaturing conditions, the binding affinity being greater than that of a reference sequence which has no particular affinity for polyester. In various embodiments, this affinity, expressed as the dissociation constant $K_d$, can be at least $10^{-3}$ mol/L, such as at least $10^{-4}$, at least $10^{-5}$, at least $10^{-6}$ or at least $10^{-7}$ mol/L.

When reference is made herein to various bonded or individual amino acid sequences, unless stated otherwise, these sequences are always expressed in the N- to C-terminal orientation. Furthermore, unless stated otherwise, the individual amino acids or amino acid sequences are bonded to one another by means of peptide bonds. Accordingly, the hyphen in the representation SEQ ID NO:1-SEQ ID NO:6-SEQ ID NO:2 means, for example, that these three sequences are fused to one another by means of peptide bonds.

In various embodiments, the peptide sequence having an affinity for polyester is directly covalently linked to the polyesterase, i.e. the first and/or last amino acid of the polyesterase is linked to a terminal amino acid of the peptide sequence by means of a peptide bond. Alternatively, the binding can also be achieved by means of a linker, in particular a peptide linker, such as a peptide linker. Suitable linkers are known in the prior art and can be static/rigid or flexible. This property is determined by the secondary structure of the linker; for example, rigid linkers can have an alpha helix as a secondary structure. In various embodiments, the peptide linker sequence is flexible and does not have a secondary structure or only has short secondary structural elements.

Typically, peptide linkers of this kind have a length of from 1 to 100 amino acids, such as from 2 to 30 amino acids, or from 5 to 25 amino acids. In various embodiments, the linker sequence is selected from AEAAAKEAAAKEAAAKA (SEQ ID NO: 6) or PPGG-NRGTTTTRRPATTTGSSPGP (SEQ ID NO:7) and homologs thereof which have at least 70%, such as 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, 98.8%, 99.0%, 99.2%, 99.4% or 99.6% sequence identity with the indicated reference sequence.

In various embodiments, this linker sequence can also contain a sequence which is recognized by a protease as a specific interface. Protease interfaces of this kind make it possible to separate the individual constituents of the polyesterase from one another, i.e. the enzyme and the peptide sequence having an affinity for polyester.

The peptide sequence having an affinity for polyester can be located at the N- and/or C-terminal relative to the polyesterase sequence. It is for the peptide sequence to be linked to the polyesterase sequence either at the C- or N-terminal; the peptide sequence is optionally linked to the C-terminus of the polyesterase, in particular by means of a peptide linker.

In various embodiments, the peptide sequence having an affinity for polyester has a length of between 5 and 200 amino acids, such as between 10 and 100 amino acids, or between 15 and 60 amino acids. The sequence can comprise several repetitions of a sequence element.

In various embodiments, the peptide sequence having an affinity for polyester is selected from antimicrobial or antifungal peptides, in particular those having a ß-pleated sheet structure, for example from tachystatins, androctonins, thanatins and bacterial antimicrobial peptides, such as LCI from *B. subtilis*. Examples of suitable peptide sequences are those which comprise or consist of at least one of the sequences given in SEQ ID NO:2 to SEQ ID NO:5 or a functional homolog thereof.

"Functional homolog," as used in this context, relates to sequences that are at least 70%, such as 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, 98.8%, 99.0%, 99.2%, 99.4% or 99.6% identical to the indicated reference sequence and have the functionality thereof, i.e. an affinity for polyester which is at least 50%, or at least 75%, of the affinity of the reference sequence.

In various embodiments, the polyesterase is linked at the C-terminal to one of the peptide linkers described above, in particular SEQ ID NO:7 or a homolog thereof, and the peptide linker is in turn linked at the C-terminal to the peptide sequence having an affinity for polyester, in particular one of the sequences of SEQ ID NO:2 to SEQ ID NO:5 or functional homologs thereof.

The following combinations are combinations, expressed in the N- to C-terminal orientation:
polyesterase SEQ ID NO:7-SEQ ID NO:2
polyesterase SEQ ID NO:7-SEQ ID NO:3
polyesterase SEQ ID NO:7-SEQ ID NO:4
polyesterase SEQ ID NO:7-SEQ ID NO:5
polyesterase SEQ ID NO:6-SEQ ID NO:2
polyesterase SEQ ID NO:6-SEQ ID NO:3
polyesterase SEQ ID NO:6-SEQ ID NO:4
polyesterase SEQ ID NO:6-SEQ ID NO:5

In various embodiments, the polyesterase is a polyesterase which has at least 70% sequence identity with the amino acid sequence given in SEQ ID NO:1, 11 or 12 over its entire length. In further embodiments, the polyesterase contained in the agent comprises or substantially consists of or consists of the amino acid sequence given in SEQ ID NO:1, 11 or 12. In various embodiments, polyesterases are derived from the amino acid sequence according to SEQ ID NO:1, 11 or 12, for example by means of mutagenesis.

In various embodiments, the polyesterase comprises an amino acid sequence which, over its entire length, is at least 70%, 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, 98.8%, 99.0%, 99.2%, 99.4% or 99.6% identical to the amino acid sequence given in SEQ ID NO:1, 11 or 12 or consists of such a sequence.

In various embodiments, the following enzymes (in the N- to C-terminal orientation) are possible:

SEQ ID NO:1-SEQ ID NO:7-SEQ ID NO:2 (SEQ ID NO:9)
SEQ ID NO:1-SEQ ID NO:7-SEQ ID NO:3
SEQ ID NO:1-SEQ ID NO:7-SEQ ID NO:4
SEQ ID NO:1-SEQ ID NO:7-SEQ ID NO:5
SEQ ID NO:1-SEQ ID NO:6-SEQ ID NO:2 (SEQ ID NO:8)
SEQ ID NO:1-SEQ ID NO:6-SEQ ID NO:3
SEQ ID NO:1-SEQ ID NO:6-SEQ ID NO:4
SEQ ID NO:1-SEQ ID NO:6-SEQ ID NO:5
SEQ ID NO:11-SEQ ID NO:7-SEQ ID NO:2
SEQ ID NO:11-SEQ ID NO:7-SEQ ID NO:3
SEQ ID NO:11-SEQ ID NO:7-SEQ ID NO:4
SEQ ID NO:11-SEQ ID NO:7-SEQ ID NO:5
SEQ ID NO:11-SEQ ID NO:6-SEQ ID NO:2
SEQ ID NO:11-SEQ ID NO:6-SEQ ID NO:3
SEQ ID NO:11-SEQ ID NO:6-SEQ ID NO:4
SEQ ID NO:11-SEQ ID NO:6-SEQ ID NO:5
SEQ ID NO:12-SEQ ID NO:7-SEQ ID NO:2
SEQ ID NO:12-SEQ ID NO:7-SEQ ID NO:3
SEQ ID NO:12-SEQ ID NO:7-SEQ ID NO:4
SEQ ID NO:12-SEQ ID NO:7-SEQ ID NO:5
SEQ ID NO:12-SEQ ID NO:6-SEQ ID NO:2
SEQ ID NO: 12-SEQ ID NO:6-SEQ ID NO:3
SEQ ID NO: 12-SEQ ID NO:6-SEQ ID NO:4
SEQ ID NO: 12-SEQ ID NO:6-SEQ ID NO:5

In various other embodiments,
(a) the polyesterase is obtainable from a polyesterase as defined above as the starting molecule by single or multiple conservative amino acid substitution; and/or
(b) the polyesterase is obtainable from a polyesterase as defined above as the starting molecule by means of fragmentation or deletion, insertion or substitution mutagenesis, and comprises an amino acid sequence which matches the starting molecule over a length of at least 210, 220, 230, 240, 245, 250, 255, 256, 257, 258, 259, 260 or 261 contiguous amino acids.

The agents contain the polyesterase in an amount of from 0.00001 to 1 wt. %, such as in an amount of from 0.0001 to 0.5 wt. %, or in an amount of from 0.001 to 0.1 wt. %, in each case based on the active protein.

The identity of nucleic acid or amino acid sequences is determined by a sequence comparison. This sequence comparison is based on the BLAST algorithm established and commonly used in the prior art (cf. for example Altschul et al. (1990): "Basic local alignment search tool," J. Mol. Biol. 215:403-410, and Altschul et al. (1997): "Gapped BLAST and PSI-BLAST: a new generation of protein database search programs;" Nucleic Acids Res. 25:3389-3402) and in principle occurs by associating similar sequences of nucleotides or amino acids in the nucleic acid or amino acid sequences. The assignment of the relevant positions shown in a table is referred to as an alignment. Another algorithm available in the prior art is the FASTA algorithm. Sequence comparisons (alignments), in particular multiple sequence comparisons, are created using computer programs. The Clustal series (cf. for example, Chenna et al. (2003) "Multiple sequence alignment with the Clustal series of programs," Nucleic Acid Res. 31:3497-3500), T-Coffee (cf. for example Notredame et al. (2000) "T-Coffee: A novel method for multiple sequence alignments," J. Mol. Biol. 302:205-217) or programs based on these programs or algorithms are frequently used, for example. Sequence comparisons (alignments) using the computer program Vector NTI® Suite 10.3 (Invitrogen Corporation, 1600 Faraday Avenue, Carlsbad, California, USA) with the predetermined, default parameters, and the AlignX module of which for sequence comparisons is based on ClustalW, are also possible.

Such a comparison also allows conclusions to be drawn regarding the similarity of the compared sequences. It is usually given in percent identity, i.e. the proportion of identical nucleotides or amino acid residues in said sequences or in an alignment of corresponding positions. The broader concept of homology takes conserved amino acid exchanges into account in the case of amino acid sequences, i.e. amino acids having similar chemical activity, since they usually perform similar chemical activities within the protein. Therefore, the similarity between the compared sequences can also be expressed in percent homology or percent similarity. Identity and/or homology information can be provided regarding whole polypeptides or genes or only regarding individual regions. Homologous or identical regions of different nucleic acid or amino acid sequences are therefore defined by matches in the sequences. Such regions often have identical functions. They can be small and comprise only a few nucleotides or amino acids. Often, such small regions perform essential functions for the overall activity of the protein. It may therefore be expedient to relate sequence matches only to individual, optionally small regions. Unless stated otherwise, however, identity or homology information in the present application relates to the entire length of the particular nucleic acid or amino acid sequence indicated.

In various embodiments, the polyesterase comprises an amino acid sequence which, over its entire length, is at least 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, 98.8%, 99.0%, 99.2%, 99.4% or 99.6% homologous to the amino acid sequence given in SEQ ID NO:1, 11 or 12.

In a further embodiment, the polyesterase is characterized in that its anti-pilling performance is not significantly reduced compared to that of a polyesterase which comprises an amino acid sequence which corresponds to the amino acid sequences given in SEQ ID NO:1, 11 or 12, i.e. has at least 70%, 75%, 80%, 85%, 90%, 95% of the reference anti-pilling performance. The anti-pilling performance can be determined in a washing system which contains a washing agent in a dosage of between 4.5 and 7.0 grams per liter of washing liquor and the polyesterase, the polyesterases to be compared being used in the same concentration (based on the active protein) and the anti-pilling performance being determined as described herein. For example, the washing process can take place for 60 minutes at a temperature of 60° C. and the water can have a water hardness between 15.5° and 16.5° (German hardness). The concentration of the polyesterase in the washing agent intended for this washing system is from 0.00001 to 1 wt. %, such as from 0.0001 to 0.5 wt. %, or from 0.001 to 0.1 wt. %, based on the active, purified protein.

A liquid washing agent for such a washing system is composed as follows (all figures in wt. %): 4.4% alkyl benzene sulfonic acid, 5.6% anionic surfactants, 2.4% $C_{12}$-$C_{18}$Na salts of fatty acids, 4.4% non-ionic surfactants, 0.2% phosphonates, 1.4% citric acid, 0.95% NaOH, 0.01% defoamer, 2% glycerol, 0.08% preservatives, 1% ethanol, 1.6% enzyme mix (protease, amylase, cellulase, mannanase)

and the remainder being demineralized water. In a non-limiting embodiment, the dosage of the liquid washing agent is between 4.5 and 6.0 grams per liter of washing liquor, for example 4.7, 4.9 or 5.9 grams per liter of washing liquor. Washing optionally takes place in a pH range between pH 8 and pH 10.5, such as between pH 8 and pH 9.

In the context, the anti-pilling performance is determined at 60° C. using a liquid washing agent as indicated above, the washing process optionally taking place for 60 minutes.

The anti-pilling performance can be tracked using visual sampling. In this case, a group of testers assigns the laundry to be examined a value on a scale of 1-5. The value=1 represents very heavily pilled laundry, while the value=5 is associated with unpilled laundry.

The activity-equivalent use of the relevant polyesterase ensures that the respective enzymatic properties, for example the anti-pilling performance, are likened even if the ratio of active substance to total protein (the values of the specific activity) diverges. In general, a low specific activity can be compensated for by adding a larger amount of protein.

Proteins can be combined into groups of immunologically related proteins by reaction with an antiserum or a specific antibody. The members of such a group are characterized by the fact that they have the same antigenic determinant recognized by an antibody. They are therefore structurally so similar that they are recognized by an antiserum or certain antibodies. The polyesterases are characterized by having at least one, two, three or four antigenic determinants matching a polyesterase used in an agent. Due to their immunological similarities, such polyesterases are structurally so similar to the polyesterases used in the agents that a similar function can also be assumed.

Further polyesterases used in the agents can have further amino acid changes, in particular amino acid substitutions, insertions or deletions, compared to the polyesterase described in SEQ ID NO:1, 11 or 12. Such polyesterases are, for example, developed by targeted genetic alteration, i.e. by mutagenesis methods, and optimized for specific applications or with regard to specific properties (for example with regard to their catalytic activity, stability, etc.). Furthermore, nucleic acids encoding the polyesterases used can be introduced into recombination approaches and thus used to generate completely new types of polyesterases or other polypeptides.

The aim is to introduce targeted mutations such as substitutions, insertions or deletions into the known molecules in order, for example, to improve the cleaning performance of enzymes. For this purpose, in particular the surface charges and/or the isoelectric point of the molecules and thus their interactions with the substrate can be altered. For instance, the net charge of the enzymes can be altered in order to influence the substrate binding, in particular for use in washing and cleaning agents. Alternatively or additionally, the stability of the polyesterase can be increased further still by one or more corresponding mutations, thereby improving its cleaning performance. Advantageous properties of individual mutations, e.g. individual substitutions, can complement one another. A polyesterase which has already been optimized with regard to specific properties, for example with regard to its activity and/or its anti-pilling performance, can therefore also be developed within the scope.

Another object is therefore an agent containing a polyesterase, which is characterized in that it is obtainable from a polyesterase as described above as the starting molecule by single or multiple conservative amino acid substitution. The term "conservative amino acid substitution" means the exchange (substitution) of one amino acid residue for another amino acid residue, with this exchange not resulting in a change to the polarity or charge at the position of the exchanged amino acid, e.g. the exchange of a nonpolar amino acid residue for another nonpolar amino acid residue. Conservative amino acid substitutions within the scope include, for example: G=A=S, I=V=L=M, D=E, N=Q, K=R, Y=F, S=T, G=A=I=V=L=M=Y=F=W=P=S=T. The homology of the polyesterases modified in this way to the polyesterase having SEQ ID NO:1, 11 or 12 is as defined above.

Alternatively or additionally, the polyesterase is characterized in that it is obtainable from a polyesterase contained in an agent as the starting molecule by fragmentation or deletion, insertion or substitution mutagenesis and comprises an amino acid sequence which matches the starting molecule over a length of at least 210, 220, 230, 240, 245, 250, 255, 256, 257, 258, 259, 260 or 261 contiguous amino acids.

In various embodiments, the polyesterases obtainable in this way also have the sequence identities defined herein of at least 70% with the sequence according to SEQ ID NO:1, 11 or 12 even after the mutagenesis/substitution.

For instance, it is possible to delete individual amino acids at the termini or in the loops of the enzyme without the hydrolytic activity being lost or diminished in the process. Furthermore, such fragmentation or deletion, insertion or substitution mutagenesis can also for example reduce the allergenicity of the enzymes concerned and thus improve their overall applicability. Advantageously, the enzymes retain their hydrolytic activity even after mutagenesis, i.e. their hydrolytic activity corresponds at least to that of the starting enzyme, i.e. in a embodiment the hydrolytic activity is at least 80%, such as at least 90%, of the activity of the starting enzyme. Other substitutions can also exhibit advantageous effects. Both single and multiple contiguous amino acids can be exchanged for other amino acids.

In various embodiments, the polyesterase can have one or more further amino acids in addition to the sequence N- or C-terminal specified in SEQ ID NO:1, 11 or 12. In certain embodiments, such N-terminal peptides can be the naturally occurring signal peptides for the polyesterase or else a single methionine residue. In embodiments of this kind, the polyesterase has, for example, the amino acid sequence given in SEQ ID NO:10. All of the embodiments disclosed above in the context of the mature polyesterase according to SEQ ID NO:1, 11 or 12 are also applicable to the polyesterase of the sequence according to SEQ ID NO:10.

An object is an agent which is characterized in that it contains a polyesterase as defined herein. The agent is a washing or cleaning agent.

Unless explicitly stated otherwise, all percentages that are cited in connection with the compositions/agents described herein relate to wt. %, in each case based on the relevant mixture/the relevant agent.

Within the scope, unless stated otherwise, fatty acids and/or fatty alcohols and/or the derivatives thereof represent branched or unbranched carboxylic acids and/or alcohols and/or the derivatives thereof having 6 to 22 carbon atoms. In particular, the oxo-alcohols or derivatives thereof which can be obtained for example in the ROELEN oxosynthesis reaction can also be correspondingly used.

Whenever alkaline earth metals are mentioned in the following as counterions for monovalent anions, this means that the alkaline earth metal is naturally only present in half the amount of the substance—sufficient to balance the charge—like the anion.

An object is an agent which is characterized in that it contains a polyesterase as defined herein. The agent is a washing or cleaning agent.

This subject matter covers all conceivable types of washing or cleaning agents, including both concentrates and undiluted agents, for use on a commercial scale, in washing machines or for hand washing. These include, for example, washing agents for textiles, carpets or natural fibers, for which the term washing agent is used. In the context, the washing and cleaning agents also include auxiliary washing agents, which are added to the actual washing agent when washing textiles manually or using a machine in order to achieve an additional effect. Furthermore, washing and cleaning agents also include textile pre-treatment and post-treatment agents, i.e. those agents with which the item of laundry is brought into contact before the actual washing cycle, for example to loosen stubborn soiling, and also those agents which give the laundry further desirable properties such as a pleasant feel, crease resistance or low static charge in a step subsequent to the actual textile wash. Inter alia, softeners are included in the last-mentioned agents.

The washing or cleaning agents, which may be in the form of powdered solids, in further-compacted particulate form, homogeneous solutions, gels or suspensions, may contain, in addition to the above-described polyesterase, all known ingredients conventional in such agents, with at least one other ingredient being present in the agent. The agents may in particular contain surfactants, builders, bleaching agents, in particular peroxygen compounds, or bleach activators. They may also contain water-miscible organic solvents, further enzymes, sequestering agents, electrolytes, pH regulators and/or further auxiliaries such as optical brighteners, graying inhibitors, foam regulators, as well as dyes and fragrances, and combinations thereof.

In particular, a combination of the agent with one or more further ingredients is advantageous, since, in embodiments, such an agent has an improved cleaning performance by virtue of resulting synergisms. In particular, combining the agent with a surfactant and/or a builder and/or a peroxygen compound and/or a bleach activator can result in such a synergism.

Advantageous ingredients of agents are disclosed in international patent application WO 2009/121725, starting at the penultimate paragraph of page 5 and ending after the second paragraph on page 13. Reference is expressly made to this disclosure and the disclosure therein is incorporated in the present patent application.

These and other aspects, features and advantages will become apparent to a person skilled in the art through the study of the following detailed description and claims. Any feature from one aspect can be used in any other aspect. Furthermore, it is readily understood that the examples contained herein are intended to describe and illustrate but not to limit the claims and that, in particular, is not limited to these examples. Unless stated otherwise, all percentages indicated are percentages by weight, based on the total weight of the composition. Numerical ranges that are indicated in the format "from x to y" also include the stated values. If several numerical ranges are indicated in this format, it is readily understood that all ranges that result from the combination of the various endpoints are also included.

In addition to the polyesterase, the agents optionally also contain at least one compound from the class of surfactants, in particular selected from anionic and non-ionic, but also cationic, zwitterionic or amphoteric surfactants.

Suitable surfactants are, for example, anionic surfactants of formula (I)

$$R—SO_3^-Y^+ \quad (I).$$

In this formula (I), R represents a linear or branched, unsubstituted alkyl aryl functional group. $Y^+$ represents a monovalent cation or the n-th part of an n-valent cation, the alkali metal ions, including $Na^+$ or $K^+$. Further cations $Y^+$ can be selected from $NH_4^+$, ½ $Zn^{2+}$, ½ $Mg^{2+}$, ½ $Ca^{2+}$, ½ $Mn^{2+}$, and mixtures thereof.

"Alkyl aryl," as used herein, refers to organic functional groups that consist of an alkyl functional group and an aromatic functional group. Typical examples of functional groups of this kind include, but are not limited to, alkylbenzene functional groups, such as benzyl, butylbenzene functional groups, nonylbenzene functional groups, decylbenzene functional groups, undecylbenzene functional groups, dodecylbenzene functional groups, tridecylbenzene functional groups, and the like.

In various embodiments, surfactants of this kind are selected from linear or branched alkylbenzene sulfonates of formula A-1

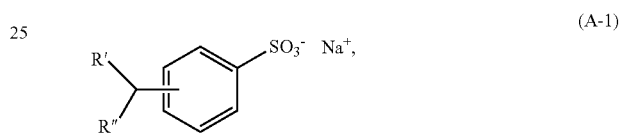

(A-1)

in which R' and R" together contain 9 to 19, such as 11 to 15, and in particular 11 to 13, C atoms. A particular representative can be described by formula A-1a:

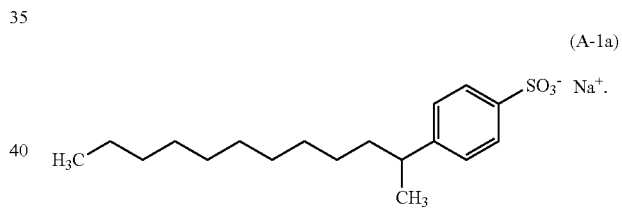

(A-1a)

In various embodiments, the compound of formula (I) is optionally the sodium salt of a linear alkylbenzene sulfonate.

In agents, the at least one compound from the class of anionic surfactants of formula (I) is contained in the washing or cleaning agent in an amount of from 0.001 to 30 wt. %, such as from 0.001 to 10 wt. %, or from 2 to 6 wt. %, or from 3 to 5 wt. %, in each case based on the total weight of the cleaning agent.

In various embodiments, the agents contain at least one anionic surfactant of the formula $$R^1—O-(AO)_n—SO_3^-X^+ \quad (II).$$

In this formula (II), $R^1$ represents a linear or branched, substituted or unsubstituted alkyl, aryl or alkyl aryl functional group, such as a linear, unsubstituted alkyl functional group, or a fatty alcohol functional group. Non-limiting functional groups $R^1$ are selected from decyl, undecyl, dodecyl, tridecyl, tetradecyl, pentadecyl, hexadecyl, heptadecyl, octadecyl, nonadecyl, eicosyl functional groups and mixtures thereof, such as the representatives having an even number of C atoms. Non-limiting functional groups $R^1$ are derived from $C_{12}$-$C_{18}$ fatty alcohols, for example from coconut fatty alcohol, tallow fatty alcohol, lauryl, myristyl, cetyl or stearyl alcohol or from $C_{10}$-$C_{20}$ oxo alcohols.

AO represents an ethylene oxide (EO) group or propylene oxide (PO) group, such as an ethylene oxide group. The index n represents an integer of from 1 to 50, or from 1 to 20, and in particular from 2 to 10. In a non-limiting embodiment, n represents the numbers 2, 3, 4, 5, 6, 7 or 8. $X^+$ represents a monovalent cation or the n-th part of an n-valent cation, the alkali metal ions, including $Na^+$ or $K+$. Further cations $X^+$ can be selected from $NH_4^+$, ½ $Zn^{2+}$, ½ $Mg^{2+}$, ½ $Ca^{2+}$, ½ $Mn^{2+}$, and mixtures thereof.

In summary, agents in various embodiments thus contain at least one anionic surfactant selected from fatty alcohol ether sulfates of formula A-2

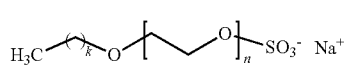 (A-2)

where k=11 to 19, and n=2, 3, 4, 5, 6, 7 or 8. Non-limiting representatives are Na—$C_{12-14}$ fatty alcohol ether sulfates having 2 EO (k=11-13, n=2 in formula A-2).

In various embodiments, the cleaning agent contains the at least one anionic surfactant of formula (II) in an amount of from 2 to 10 wt. %, such as from 3 to 8 wt. %, based on the total weight of the cleaning agent.

Other anionic surfactants that can be used are the alkyl sulfates of the formula $$R^2\text{—O—}SO_3^-X^+ \quad (III).$$

In this formula (III), $R^2$ represents a linear or branched, substituted or unsubstituted alkyl functional group, such as a linear, unsubstituted alkyl functional group, or a fatty alcohol functional group. Non-limiting functional groups $R^2$ are selected from decyl, undecyl, dodecyl, tridecyl, tetradecyl, pentadecyl, hexadecyl, heptadecyl, octadecyl, nonadecyl, eicosyl functional groups and mixtures thereof, such as the representatives having an even number of C atoms. Non-limiting functional groups $R^2$ are derived from $C_{12}$-$C_{18}$ fatty alcohols, for example from coconut fatty alcohol, tallow fatty alcohol, lauryl, myristyl, cetyl or stearyl alcohol or from $C_{10}$-$C_{20}$ oxo alcohols. $X^+$ represents a monovalent cation or the n-th part of an n-valent cation, the alkali metal ions, including $Na^+$ or $K^+$. Further cations $X^+$ can be selected from $NH_4^+$, ½ $Zn^{2+}$, ½ $Mg^{2+}$, ½ $Ca^{2+}$, ½ $Mn^{2+}$, and mixtures thereof.

In various embodiments, these surfactants are selected from fatty alcohol sulfates of formula A-3

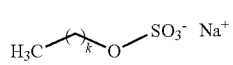 (A-3)

where k=11 to 19. Non-limiting representatives are Na—$C_{12-14}$ fatty alcohol sulfates (k=11-13 in formula A-3).

In various embodiments, the agent can contain, in addition to the anionic surfactants described above, in particular those of formulas (I) to (III), or alternatively at least one other surfactant. Alternative or additional surfactants are, in particular, further anionic surfactants, non-ionic surfactants and mixtures thereof, but also cationic, zwitterionic and amphoteric surfactants.

In various embodiments, the agents comprise at least one non-ionic surfactant, in particular at least one fatty alcohol alkoxylate.

Suitable non-ionic surfactants are those of the formula $$R^3\text{—O-}(AO)_m\text{—H} \quad (IV),$$

in which $R^3$ represents a linear or branched, substituted or unsubstituted alkyl functional group, AO represents an ethylene oxide (EO) or propylene oxide (PO) group and m represents integers from 1 to 50.

In the aforementioned formula (IV), $R^3$ represents a linear or branched, substituted or unsubstituted alkyl functional group, such as a linear, unsubstituted alkyl functional group, or a fatty alcohol functional group. Non-limiting functional groups $R^2$ are selected from decyl, undecyl, dodecyl, tridecyl, tetradecyl, pentadecyl, hexadecyl, heptadecyl, octadecyl, nonadecyl, eicosyl functional groups and mixtures thereof, such as the representatives having an even number of C atoms. Non-limiting functional groups $R^3$ are derived from $C_{12}$-$C_{18}$ fatty alcohols, for example from coconut fatty alcohol, tallow fatty alcohol, lauryl, myristyl, cetyl or stearyl alcohol or from $C_{10}$-$C_{20}$ oxo alcohols.

AO represents an ethylene oxide (EO) group or propylene oxide (PO) group, such as an ethylene oxide group. The index m represents an integer from 1 to 50, or from 1 to 20, and in particular from 2 to 10. In a non-limiting embodiment, m represents the numbers 2, 3, 4, 5, 6, 7 or 8.

In summary, the fatty alcohol alkoxylates to be optionally used are compounds of the formula

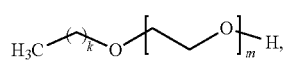 (V)

where k=11 to 19, and m=2, 3, 4, 5, 6, 7 or 8. Non-limiting representatives are $C_{12-18}$ fatty alcohols having 7 EO (k=11-17, m=7 in formula (V)).

Further non-ionic surfactants which can be contained in the described agents within the meaning include, but are not limited to, alkyl glycosides, alkoxylated fatty acid alkyl esters, amine oxides, fatty acid alkanolamides, hydroxy mixed ethers, sorbitan fatty acid esters, polyhydroxy fatty acid amides and alkoxylated alcohols.

Suitable amphoteric surfactants are, for example, betaines of formula $(R^{iii})(R^{iv})(R^{v})N^+CH_2COO^-$, in which $R^{iii}$ denotes an alkyl functional group, which is optionally interrupted by heteroatoms or heteroatom groups, having 8 to 25, such as 10 to 21, carbon atoms, and $R^{iv}$ and $R^v$ denote identical or different alkyl functional groups having 1 to 3 carbon atoms, in particular $C_{10}$-$C_{18}$ alkyl dimethyl carboxymethyl betaine and $C_{11}$-$C_{17}$ alkyl amido propyl dimethyl carboxymethyl betaine.

Suitable cationic surfactants are, inter alia, the quaternary ammonium compounds of formula $(R^{vi})(R^{vii})(R^{viii})(R^{ix})N^+ X^-$, in which $R^{vi}$ to $R^{ix}$ denote four identical or different, and in particular two long-chain and two short-chain, alkyl functional groups, and X denotes an anion, in particular a halide ion, for example didecyl dimethyl ammonium chloride, alkyl benzyl didecyl ammonium chloride and mixtures thereof. Further suitable cationic surfactants are the quaternary surface-active compounds, in particular having a sulfonium, phosphonium, iodonium or arsonium group, which are also known as antimicrobial active ingredients. By using quaternary surface-active compounds having an antimicrobial action, the agent can be designed having an antimicrobial effect or the antimicrobial effect thereof, which may already be present due to other ingredients, can be improved.

In various embodiments, the total amount of surfactants based on the weight of the agent is from 2 to 30 wt. %, such as from 5 to 25 wt. %, or from 10 to 20 wt. %, or from 14 to 18 wt. %, the (linear) alkylbenzene sulfonates being present at most in an amount of from 0.001 to 30 wt. %, such as from 0.001 to 10 wt. %, such as from 2 to 6 wt. %, or from 3 to 5 wt. %, based on the weight of the agent.

Washing or cleaning agents can contain further enzymes in addition to the polyesterase. These may be hydrolytic enzymes or other enzymes in a concentration that is expedient for the effectiveness of the agent. One embodiment thus represents agents which comprise one or more enzymes. All enzymes which can develop catalytic activity in the agent, in particular a protease, amylase, cellulase, hemicellulase, mannanase, tannanase, xylanase, xanthanase, xyloglucanase, ß-glucosidase, pectinase, carrageenanase, perhydrolase, oxidase, oxidoreductase or a lipase, and mixtures thereof, can be used as the enzymes. Enzymes are contained in the agent advantageously in an amount of from $1 \times 10^{-8}$ to 5 wt. % in each case, based on the active protein. Each enzyme is contained in agents in an amount of from $1 \times 10^{-7}$ to 3 wt. %, from 0.00001 to 1 wt. %, from 0.00005 to 0.5 wt. %, from 0.0001 to 0.1 wt. % or from 0.0001 to 0.05 wt. %, based on the active protein. In a non-limiting embodiment, the enzymes exhibit synergistic cleaning performance on specific stains or spots, i.e. the enzymes contained in the agent composition support one another in their cleaning performance. Synergistic effects can arise not only between different enzymes, but also between one or more enzymes and other ingredients of the agent.

The amylase(s) is/are an α-amylase. The hemicellulase is a ß-glucanase, a pectinase, a pullulanase and/or a mannanase. The cellulase is a cellulase mixture or a single-component cellulase, such as an endoglucanase and/or a cellobiohydrolase. The oxidoreductase is optionally an oxidase, in particular a choline-oxidase, or a perhydrolase.

The proteases used are optionally alkaline serine proteases. They act as unspecific endopeptidases, i.e. they hydrolyze any acid amide bonds that are inside peptides or proteins and thereby remove protein-containing stains on the item to be cleaned. Their pH optimum is usually in the highly alkaline range.

The protein concentration can be determined using known methods, for example the BCA method (bicinchoninic acid; 2,2'-bichinolyl-4,4'-dicarboxylic acid) or the Biuret method. The active protein concentration is determined by titrating the active centers using a suitable irreversible inhibitor (e.g. phenylmethylsulfonylfluoride (PMSF) for proteases) and determining the residual activity (cf. M. Bender et al. (1966), J. Am. Chem. Soc. 88(24):5890-5913).

In the cleaning agents described herein, the enzymes to be used may furthermore be formulated together with accompanying substances, for example from fermentation. In liquid formulations, the enzymes are used as enzyme liquid formulations.

The enzymes are generally not made available in the form of the pure protein, but rather in the form of stabilized, storable and transportable preparations. These pre-formulated preparations include, for example, the solid preparations obtained through granulation, extrusion, or lyophilization or, in particular in the case of liquid or gel agents, solutions of the enzymes, advantageously maximally concentrated, low-water, and/or supplemented with stabilizers or other auxiliaries.

Alternatively, the enzymes can also be encapsulated, for both the solid and the liquid administration form, for example by spray-drying or extrusion of the enzyme solution together with a natural polymer or in the form of capsules, for example those in which the enzymes are enclosed in a set gel, or in those of the core-shell type, in which an enzyme-containing core is coated with a water-, air-, and/or chemical-impermeable protective layer. Other active ingredients such as stabilizers, emulsifiers, pigments, bleaching agents, or dyes can additionally be applied in overlaid layers. Such capsules are applied using inherently known methods, for example by shaking or roll granulation or in fluidized bed processes. Such granules are advantageously low in dust, for example due to the application of polymeric film-formers, and stable in storage due to the coating.

Moreover, it is possible to formulate two or more enzymes together, such that a single granule exhibits a plurality of enzyme activities.

In various embodiments, the agent can comprise one or more enzyme stabilizers. Therefore, the agent may further comprise an enzyme stabilizer, for example selected from the group consisting of sodium formate, sodium sulfate, lower aliphatic alcohols and boric acid as well as contain esters and salts thereof. Of course, two or more of these compounds can also be used in combination. The salts of the compounds mentioned can also be used in the form of hydrates, such as sodium sulfate decahydrate.

The term "lower aliphatic alcohols," as used herein, includes monoalcohols, diols and polyhydric alcohols having up to 6 carbon atoms. In this context, in particular polyols, for example glycerol, (mono)ethylene glycol, (mono)propylene glycol or sorbitol, should be mentioned as belonging to the group of lower aliphatic alcohols, without the claims being restricted thereto.

In addition to the at least one enzyme stabilizer selected from the above group, an agent can also contain at least one further stabilizer. Such stabilizers are known in the prior art.

Reversible protease inhibitors protect the enzymes contained in a washing or cleaning agent from proteolytic degradation by reversibly inhibiting the enzymatic activity of the proteases contained in the agent. Benzamidine hydrochloride, boronic acids or their salts or esters are frequently used as reversible protease inhibitors, including above all derivatives having aromatic groups, for example ortho-, meta- or para-substituted phenylboronic acids, in particular 4-formylphenylboronic acid, or the salts or esters of the mentioned compounds. Peptide aldehydes, that is to say oligopeptides having a reduced C-terminus, in particular those of 2 to 50 monomers, are also used for this purpose. Peptide reversible protease inhibitors include, inter alia, ovomucoid and leupeptin.

Other enzyme stabilizers are amino alcohols such as mono-, di-, triethanol- and -propanolamine and mixtures thereof, aliphatic carboxylic acids up to $C_{12}$, such as succinic acid, other dicarboxylic acids or salts of the mentioned acids. End-capped fatty acid amide alkoxylates are also suitable for this purpose. Some organic acids used as builders can also stabilize an enzyme. Calcium and/or magnesium salts are also used for this purpose, for example calcium acetate.

Polyamide oligomers or polymeric compounds such as lignin, water-soluble vinyl copolymers or cellulose ethers, acrylic polymers and/or polyamides stabilize the enzyme preparation against physical influences or pH fluctuations, among other things. Polymers containing polyamine N-oxide act simultaneously as enzyme stabilizers and as color transfer inhibitors. Other polymeric stabilizers are linear $C_8$-$C_{18}$ polyoxyalkylenes. Alkyl polyglycosides can also stabilize the enzymatic components of the agent and are capable of additionally increasing their performance. Cross-linked N-containing compounds fulfill a double function as soil release agents and as enzyme stabilizers. A hydrophobic, non-ionic polymer stabilizes in particular any cellulase that may be contained.

Reducing agents and antioxidants increase the stability of the enzymes against oxidative decay; for this purpose, sulfur-containing reducing agents are common, such as sodium sulfite and reducing sugars.

In one embodiment, the agents are liquid and contain water as the main solvent, i.e. they are aqueous agents. The water content of the aqueous agent is usually from 15 to 70 wt. %, such as from 20 to 60 wt. %. In various embodiments, the water content is more than 5 wt. %, or more than 15 wt. % or more than 50 wt. %, in each case based on the total amount of agent.

In addition, non-aqueous solvents can be added to the agent. Suitable non-aqueous solvents include monovalent or polyvalent alcohols, alkanol amines or glycol ethers, if they can be mixed with water in the stated concentration range. In a non-limiting embodiment, the solvents are selected from ethanol, n-propanol, i-propanol, butanols, glycol, propanediol, butanediol, methylpropanediol, glycerol, diglycol, propyl diglycol, butyl diglycol, hexylene glycol, ethylene glycol methyl ether, ethylene glycol ethyl ether, ethylene glycol propyl ether, ethylene glycol mono-n-butyl ether, diethylene glycol methyl ether, diethylene glycol ethyl ether, propylene glycol methyl ether, propylene glycol ethyl ether, propylene glycol propyl ether, dipropylene glycol mono methyl ether, dipropylene glycol mono ethyl ether, methoxytriglycol, ethoxytriglycol, butoxytriglycol, 1-butoxyethoxy-2-propanol, 3-methyl-3-methoxybutanol, propylene-glycol-t-butylether, di-n-octylether, and mixtures of these solvents.

The one or more non-aqueous solvents are usually contained in an amount of from 0.1 to 10 wt. %, such as from 1 to 8 wt. %, based on the total composition.

In addition to the components mentioned so far, the agents can contain other ingredients that further improve the practical and/or aesthetic properties of the cleaning agent. These include, for example, additives for improving the flow and drying behavior, for adjusting the viscosity, and/or for stabilization and other auxiliary and additional substances that are customary in cleaning agents, such as UV stabilizers, perfume, pearlescing agents, dyes, corrosion inhibitors, preservatives, bitterns, organic salts, disinfectants, structuring polymers, encapsulated ingredients (e.g. encapsulated perfume), pH adjusters and skin-feel-improving or nourishing additives.

An agent, in particular a washing or cleaning agent, such as contains at least one water-soluble and/or water-insoluble, organic and/or inorganic builder.

The builders that can generally be used include, in particular, the aminocarboxylic acids and their salts, zeolites, silicates, carbonates, organic (co)builders and—where there are no ecological prejudices against their use—also the phosphates. However, the agents are phosphate-free.

The water-soluble organic builders include polycarboxylic acids, in particular citric acid and saccharic acids, monomeric and polymeric aminopolycarboxylic acids, in particular methylglycinediacetic acid, nitrilotriacetic acid, ethylenediaminetetraacetic acid and polyaspartic acid, polyphosphonic acids, in particular amino tris(methylenephosphonic acid), ethylenediamine tetrakis(methylenephosphonic acid) and 1-hydroxyethane-1,1-diphosphonic acid, polymeric hydroxy compounds such as dextrin, and polymeric (poly)carboxylic acids, polymeric acrylic acids, methacrylic acids, maleic acids, and mixed polymers thereof, which may also contain, in the polymer, small portions of polymerizable substances, without a carboxylic acid functionality. Compounds of this class which are suitable are copolymers of acrylic acid or methacrylic acid with vinyl ethers, such as vinyl methyl ethers, vinyl esters, ethylene, propylene, and styrene, in which the proportion of the acid is at least 50 wt. %. The organic builders may, in particular for the production of liquid agents, be used in the form of aqueous solutions, such as in the form of 30 to 50 wt. % aqueous solutions. All mentioned acids are generally used in the form of the water-soluble salts thereof, in particular the alkali salts thereof.

Organic builders, if desired, can be contained in amounts of up to 40 wt. %, in particular up to 25 wt. %, or from 1 to 8 wt. %. Amounts close to the stated upper limit are used in paste-form or liquid, in particular water-containing, agents. Laundry post-treatment agents, such as softeners, can optionally also be free of organic builders.

Suitable water-soluble inorganic builder materials are, in particular, alkali silicates and, if there are no concerns about their use, also polyphosphates, such as sodium triphosphate. In particular crystalline or amorphous alkali aluminosilicates, if desired, can be used as water-insoluble, water-dispersible inorganic builder materials in amounts of up to 50 wt. %, such as no greater than 40 wt. %, and in liquid agents in particular in amounts of from 1 to 5 wt. %. Among these, crystalline sodium aluminosilicates of washing agent quality, in particular zeolite A, P and optionally X, are optional. Amounts close to the stated upper limit are used in solid particulate agents. Suitable aluminosilicates have in particular no particles having a particle size greater than 30 μm and comprise at least 80 wt. % of particles having a size smaller than 10 μm.

Suitable substitutes or partial substitutes for the stated aluminosilicate are crystalline alkali silicates, which may be present alone or in a mixture with amorphous silicates. The alkali silicates that can be used in the agents as builders have a molar ratio of alkali oxide to $SiO_2$ of less than 0.95, in particular from 1:1.1 to 1:12, and may be present in amorphous or crystalline form. Non-limiting alkali silicates are sodium silicates, in particular amorphous sodium silicates having a $Na_2O:SiO_2$ molar ratio of from 1:2 to 1:2.8. Crystalline phyllosilicates of general formula $Na_2Si_xO_{2x+1} \cdot y\, H_2O$, where x, referred to as the module, is a number from 1.9 to 4, y is a number from 0 to 20, and values for x are 2, 3 or 4, are used as crystalline silicates, which may be present alone or in a mixture with amorphous silicates. Non-limiting crystalline phyllosilicates are those in which x in the stated general formula assumes the values 2 or 3. In particular, both beta-sodium and delta-sodium disilicates ($Na_2Si_2O_5 \cdot y\, H_2O$) are possible. Practically water-free crystalline alkali silicates of the above general formula, in which x is a number from 1.9 to 2.1, which alkali silicates are produced from amorphous alkali silicates, may also be used in agents. In a further embodiment of agents, a crystalline sodium phyllosilicate having a module of from 2 to 3, as can be produced from sand and soda, is used. Crystalline sodium silicates having a module in the range of from 1.9 to 3.5 are used in a further embodiment of agents. If alkali aluminosilicate, in particular zeolite, is also present as an additional builder, the weight ratio of aluminosilicate to silicate, in each case based on water-free active substances, is such as from 1:10 to 10:1. In agents containing both amorphous and crystalline alkali silicates, the weight ratio of amorphous alkali silicate to crystalline alkali silicate is such as from 1:2 to 2:1 and in particular from 1:1 to 2:1.

Builders are, if desired, such as contained in the agents in amounts of up to 60 wt. %, in particular from 5 wt. % to 40 wt. %. Water-soluble builders are in liquid formulations. Laundry post-treatment agents, for example softeners, are optionally free of inorganic builders.

Polymeric thickening agents within the meaning are the polycarboxylates which have a thickening action as polyelectrolytes, such as homo- and copolymerizates of acrylic acid, in particular acrylic acid copolymers such as acrylic acid-methacrylic acid copolymers, and the polysaccharides, in particular heteropolysaccharides, and other conventional thickening polymers. Suitable polysaccharides or heteropolysaccharides are the polysaccharide gums, for example gum arabic, agar, alginates, carrageenans and their salts, guar, guar gum, tragacanth, gellan, ramsan, dextran or xanthan and their derivatives, for example propoxylated guar, and mixtures thereof. Other polysaccharide thickeners, such as starches or cellulose derivatives, may alternatively or be used in addition to a polysaccharide gum, for example starches of various origins and starch derivatives, for example hydroxyethyl starch, starch phosphate esters or starch acetates, or carboxymethyl cellulose or its sodium salt, methyl, ethyl, hydroxyethyl, hydroxypropyl, hydroxypropylmethyl or hydroxyethylmethyl cellulose or cellulose acetate.

Acrylic acid polymers suitable as polymeric thickening agents are, for example, high-molecular-weight homopolymers of acrylic acid (INCI: carbomer) which are cross-linked with a polyalkenyl polyether, in particular an allyl ether of sucrose, pentaerythritol or propylene, and also referred to as carboxyvinyl polymers.

However, particularly suitable polymeric thickening agents are the following acrylic acid copolymers: (i) copolymers of two or more monomers from the group of acrylic acid, methacrylic acid and their simple esters, such as formed by $C_{1-4}$ alkanols (INCI: acrylates copolymer), which include, for example, the copolymers of methacrylic acid, butyl acrylate and methyl methacrylate (CAS 25035-69-2) or butyl acrylate and methyl methacrylate (CAS 25852-37-3); (ii) cross-linked high-molecular-weight acrylic acid copolymers, which include, for example, the copolymers of $C_{10-30}$ alkyl acrylates cross-linked with an allyl ether of sucrose or pentaerythritol with one or more monomers from the group of acrylic acid, methacrylic acid and their simple esters, such as formed by $C_{1-4}$ alkanols (INCI: acrylates/$C_{10-30}$ alkyl acrylate crosspolymer).

The content of polymeric thickening agent is usually no more than 8 wt. %, such as between 0.1 and 7 wt. %, or between 0.5 and 6 wt. %, in particular between 1 and 5 wt. % or 1.5 and 4 wt. %, for example between 2 and 2.5 wt. %, based on the total weight of the agent.

To stabilize the agent, in particular at a high surfactant content, one or more dicarboxylic acids and/or their salts can be added, in particular a composition of Na salts of adipic, succinic and glutaric acid, for example as is available under the trade name Sokalan® DSC. The use here is advantageously in amounts of from 0.1 to 8 wt. %, such as from 0.5 to 7 wt. %, in particular from 1.3 to 6 wt. % or from 2 to 4 wt. %, based on the total weight of the cleaning agent.

However, if the use thereof can be dispensed with, the agent free of dicarboxylic acids (dicarboxylic acid salts).

The washing agents can be compared with reference washing agents in order to determine the increased anti-pilling performance of the agents. A washing system of this kind may be composed as follows (all figures in wt. %): reference agent: 4.4% alkyl benzene sulfonic acid, 5.6% further anionic surfactants, 2.4% $C_{12}$-$C_{18}$Na salts of fatty acids (soaps), 4.4% non-ionic surfactants, 0.2% phosphonates, 1.4% citric acid, 0.95% NaOH, 0.01% defoamer, 2.0% glycerol, 0.08% preservatives, 1% ethanol, 1.6% enzyme mix (protease, amylase, cellulase, mannanase) and the remainder being demineralized water; agent: 4.4% alkyl benzene sulfonic acid, 5.6% further anionic surfactants, 2.4% $C_{12}$-$C_{18}$Na salts of fatty acids (soaps), 4.4% non-ionic surfactants, 0.2% phosphonates, 1.4% citric acid, 0.95% NaOH, 0.01% defoamer, 2.0% glycerol, 0.08% preservatives, 1% ethanol, 1.6% enzyme mix (protease, amylase, cellulase, mannanase), 0.009% polyesterase and the remainder being demineralized water. In a non-limiting embodiment, the dosage of the liquid washing agent is between 4.5 and 6.0 grams per liter of washing liquor, for example 4.7, 4.9 or 5.9 grams per liter of washing liquor. Washing takes place in a pH range between pH 8 and pH 10.5, such as between pH 8 and pH 9.

The previously mentioned embodiments include all solid, powdered, liquid, gel or pasty administration forms of agents, which may optionally also consist of a plurality of phases and can be present in compressed or uncompressed form. The agent may be present as a flowable powder, in particular having a bulk density of from 300 g/l to 1200 g/l, in particular from 500 g/l to 900 g/l or from 600 g/l to 850 g/l. The solid administration forms of the agent also include extrudates, granules, tablets or pouches. Alternatively, the agent may also be in liquid, gel or pasty form, for example in the form of a non-aqueous liquid washing agent or a non-aqueous paste or in the form of an aqueous liquid washing agent or a water-containing paste. The agent may also be present as a single-component system. Such agents consist of one phase. Alternatively, an agent may also consist of a plurality of phases. Such an agent is therefore divided into a plurality of components (multi-component system).

The method for cleaning textiles, is characterized in that an agent is used in at least one method step. The textiles contain or consist of polyester.

In various embodiments, the method described above is characterized in that the agent is used at a temperature of from 0 to 100° C., such as from 0 to 80° C., or from 30 to 70° C. or at 40 or 60° C.

These include both manual and mechanical methods. Methods for cleaning textiles are generally characterized by the fact that, in a plurality of method steps, various cleaning-active substances are applied to the material to be cleaned and washed off after the exposure time, or in that the material to be cleaned is otherwise treated with a washing agent or a solution or dilution of this agent. All conceivable washing or cleaning methods can be enhanced in at least one of the method steps by the use of a washing or cleaning agent, and therefore represent embodiments. All aspects, objects and embodiments described for agents are also applicable to this subject matter. Therefore, reference is expressly made at this juncture to the disclosure at the corresponding point when it was indicated that this disclosure also applies to the above-described methods.

Since enzymes naturally already have catalytic activity and also exhibit this in media which otherwise have no cleaning power, for example in a simple buffer, a single and/or the sole step of such a method can consist in a polyesterase, which is the only cleaning-active component, being brought into contact with the stain, such as in a buffer solution or in water. This constitutes a further embodiment of this subject matter.

Alternative embodiments of this subject matter are also represented by methods for treating textile raw materials or for textile care, in which an agent becomes active in at least one method step. Among these, methods for textile raw materials, fibers or textiles with synthetic constituents are optional, and very particularly for those with polyester.

Moreover, the use of the agent is described herein, for example as washing or cleaning agents as described above, for the (improved) removal of stains, for example from textiles, in particular polyester textiles.

Finally, the use of a polyesterase is also for reducing the pilling effects of an agent, such as a washing agent, or a liquid washing agent, the agent containing the polyesterase. The polyesterase is a polyesterase as defined herein. In various embodiments of the use, the polyesterase is contained in the agent in an amount of from 0.00001 to 1 wt. %, such as in an amount of from 0.0001 to 0.5 wt. %, or in an amount of from 0.001 to 0.1 wt. %. In further various embodiments, the polyesterase, which brings about a reduction in the pilling effect, is applied to textiles, in particular textiles which consist of polyester or comprise polyester.

All aspects, objects and embodiments described for agents and the polyesterase are also applicable to the further subjects. Therefore, reference is expressly made at this juncture to the disclosure at the corresponding point when it was indicated that this disclosure also applies to the above-described methods and the uses.

EXAMPLES

Example 1: Expression of a Polyesterase in the Filamentous Ascomycete *Trichoderma reesei*

A synthetic gene with a nucleotide sequence adapted to the *Trichoderma* codon usage was used for the expression of the polyesterase. The gene was fused with various secretion signals and anchor peptides using Gibson assembly and cloned into a plasmid for amplification in *Escherichia coli*. This expression plasmid has a strong promoter for the expression of the corresponding mRNA of the polyesterase gene and further elements which allow a selection of *Escherichia coli* cells which have taken up the expression construct after the transformation.

The corresponding construct for transformation and subsequent integration into the genome of *Trichoderma reesei* was obtained from this plasmid by restriction with NotI. This transformation fragment contains the elements for the expression of the polyesterase gene and a gene which allows the selection of successfully transformed cells in *Trichoderma reesei*.

After the most productive expression strain had been selected, the polyesterase was produced in sufficient quantity by fermentation in order to be able to be used for washing application tests. The following construct was produced from the polyesterase, linker and peptide anchor: SEQ ID NO:1-SEQ ID NO:6-SEQ ID NO:2

Example 2: Wash Test

Washing Agent Matrix Used

This is a commercially available washing agent matrix that was used for the wash test:

| Chemical name | Wt. % of active substance in the raw material | Wt. % of active substance in the formulation |
| --- | --- | --- |
| Demineralized water | 100 | Remainder |
| Alkyl benzene sulfonic acid | 96 | 3-7 |
| Anionic surfactants (FAEOS) | 70 | 2-6 |

-continued

| Chemical name | Wt. % of active substance in the raw material | Wt. % of active substance in the formulation |
| --- | --- | --- |
| C12-C18 fatty acid Na salt | 30 | 0.3-1 |
| Non-ionic surfactants (FAEO) | 100 | 3-7 |
| Phosphonates | 40 | 0.1-0.8 |
| Citric acid | 100 | 0.1-2 |
| NaOH | 50 | 0.3-1 |
| Defoamer | t.q. | 0.005-0.01 |
| Glycerol | 99.5 | 0.3-1 |
| Preservatives | 100 | 0.05-0.1 |
| Boric acid | 100 | 0.3-1 |
| Optical brightener | 90 | 0.01-0.08 |
| Thickener | 25 | 1-3 |
| Enzymes (except polyesterase) | 100 | 0.5-2 |
| Dye, perfume | | q.s. |

Dosage 50 ml

Wash Test to Determine the Anti-Pilling Performance of Enzymes 20 identical tests are carried out in succession in a commercially available washing machine. Various polyesters and blended textiles are used as textiles to be assessed, some of which are new and some of which are pre-pilled. After the 20 tests, the pill reduction of the pre-pilled fabrics and the pill formation of the new fabrics are assessed visually.

The pre-pilled fabrics are produced by washing cycles repeated 20 times at 40° C. in commercially available washing machines.

After each washing cycle, the complete laundry is dried in the dryer.

Washing Conditions:

Water with 16° dH, 2.5 kg clean filling laundry, 40° C. normal program, 50 ml washing agent as described above per machine Dosage of the polyesterase to be examined: 50 mg active enzyme per washing machine Sample 1: only washing agent as described above (comparison reference)

Sample 2: washing agent+50 mg polyesterase (SEQ ID NO:1)

Sample 3: washing agent+10 mg polyesterase (SEQ ID NO:1)

Sample 2: washing agent+10 mg polyesterase (SEQ ID NO:1+SEQ ID NO:6+SEQ ID NO:2; i.e. the polyesterase sequence SEQ ID NO:1 is linked at the C-terminal to a linker according to SEQ ID NO:6 by means of a peptide bond, which linker is in turn linked at the C-terminal to the sequence according to SEQ ID NO:2 by means of a peptide bond;)

Result after 20 washes on:

A=100% polyester textile, WFK30A (wfk cleaning technology institute e. V.), new

B=80% cotton/20% polyester textile, HS pink yard good (HS Stoffe GmbH & Co. KG), pre-pilled Visual sampling of the pills, scale 1-5, very strongly pilled=1, not pilled=5

| Sample | Textile A | Textile B |
| --- | --- | --- |
| 1 | 1.6 | 2.4 |
| 2 | 2.4 | 2.9 |

-continued

| Sample | Textile A | Textile B |
|---|---|---|
| 3 | 2.1 | 2.6 |
| 4 | 2.6 | 3.7 |

A change of 0.5 units can be considered significant.

The polyesterase significantly improves the pill appearance both compared with the washing agent without a polyesterase and the polyesterase without a peptide sequence having an affinity for polyester.

Example 3: Polyester-Binding Capacity

Using the enhanced green fluorescent protein (eGFP), various peptide sequences were examined for their affinity for polyester. 100% PES fabric (WFK30A) and cotton/PES blended fabric (35% cotton/65% polyester; WFK20A) were examined as the polyester.

The sequences to be tested were as follows (N- to C-terminal orientation):

Construct 1: eGFP-SEQ ID NO:6-SEQ ID NO:3
Construct 2: eGFP-SEQ ID NO:6-SEQ ID NO:4
Construct 3: eGFP-SEQ ID NO:6-SEQ ID NO:2
Construct 4: eGFP-SEQ ID NO:6-SEQ ID NO:5

The fusion proteins were cloned in *Escherichia coli* and produced in the microtiter plate (MTP, 96-well), the cells were digested with lysozyme and the cell-free extract of the individual fusion proteins was isolated.

Before the binding test, the fluorescence of the fusion proteins (cell-free extract) was normalized to 100,000 RFU.

Sample textiles were cut into small pieces (approx. 0.5× 0.5 mm) and placed in individual wells of a filter plate.

100 µl of cell-free extract was applied to the textile sample using a pipette and bound there for 10 minutes.

The cell-free extract was removed by means of a centrifugation step and the textile samples were washed three times with a buffer (100 mM Tris-HCl, pH 8.0) (by 3×5 min shaking and 5 min centrifugation).

Finally, the samples were washed with a surfactant (0.5 mM sodium dodecylbenzenesulfonate (LAS), pH 8.0) and dried (by 1×5 min shaking and 5 min centrifugation).

The samples were visually assessed with regard to their fluorescence using a confocal microscope (TCS SP8, Leica Microsystems CMS GmbH) (0=no fluorescence; −/+=weak fluorescence; +=fluorescence; ++=strong fluorescence; +++=very strong fluorescence).

Untreated and only eGFP-treated samples demonstrated no or hardly any detectable fluorescence. By contrast, all samples treated with the test constructs described demonstrated strong to very strong fluorescence.

| Construct | WFK30A | WFK20A |
|---|---|---|
| 1 | + | +++ |
| 2 | + | +++ |
| 3 | +++ | +++ |
| 4 | +++ | +++ |

The invention claimed is:

1. An agent, comprising:
    a polyesterase covalently bonded to at least one heterologous peptide sequence;
    wherein the at least one heterologous peptide sequence has an affinity for polyesters; and,
wherein the agent comprises the polyesterase in an amount ranging from 0.00001 to 1 wt. %.

2. The agent according to claim 1, wherein the at least one peptide sequence is selected from antimicrobial peptides, antifungal peptides, or combination thereof.

3. The agent according to claim 2, wherein the at least one peptide sequence is selected from peptide sequences comprising or consisting of at least one sequence selected from SEQ ID NO:2, SEQ ID NO:3, SEQ ID NO:4, SEQ ID NO:5, combinations thereof, or functional homolog thereof.

4. The agent according to claim 1 wherein
    the at least one peptide sequence has a length ranging from 5 to 200 amino acids,
    the at least one peptide sequence is located at the N-terminal and/or C-terminal relative to the polyesterase sequence; and combinations thereof.

5. The agent according to claim 1 wherein the at least one peptide sequence is covalently bonded to the polyesterase with a linker.

6. The agent according to claim 5, wherein the peptide linker;
    has a length ranging from 1 to 100 amino acids
    is selected from AEAAAKEAAAKEAAAKA (SEQ ID NO: 6 PPGGNRGTTTTRRPATTTGSSPGP (SEQ ID NO:7), or homologs thereof; or combinations thereof.

7. The agent according to claim 1 wherein the polyesterase has the following structure in the N-terminal to C-terminal orientation:
    (i) polyesterase-SEQ ID NO:7-SEQ ID NO:2;
    (ii) polyesterase-SEQ ID NO:7-SEQ ID NO:3;
    (iii) polyesterase-SEQ ID NO:7-SEQ ID NO:4;
    (iv) polyesterase-SEQ ID NO:7-SEQ ID NO:5;
    (v) polyesterase-SEQ ID NO:6-SEQ ID NO:2;
    (vi) polyesterase-SEQ ID NO:6-SEQ ID NO:3;
    (vii) polyesterase-SEQ ID NO:6-SEQ ID NO:4; or
    (viii) polyesterase-SEQ ID NO:6-SEQ ID NO 5.

8. The agent according to claim 1, wherein the polyesterase comprises an amino acid sequence which, over its entire length, is at least 95% or more identical to the amino acid sequence given in SEQ ID NO: 1, SEQ ID NO: 11, or SEQ ID NO: 12.

9. A method for cleaning textiles, wherein the method comprises:

applying an agent to one or more textiles; wherein the agent is in accordance with the agent of claim 1.

10. The method according to claim 9, wherein the textiles comprise or consist of polyester.

11. The method of claim 9, wherein the one or more textiles comprise one or more polyester-containing textiles.

12. The method of claim 9, further comprising reducing pilling effects, increasing the anti-graying effect of an agent, and combinations thereof.

13. The method according to claim 12, wherein the at least one peptide sequence is selected from antimicrobial peptides, antifungal peptide, or combinations thereof.

14. The method according to claim 9, wherein the at least one peptide sequence is selected from peptide sequences comprising or consisting of at least one sequence selected from SEQ ID NO:2, SEQ ID NO:3, SEQ ID NO:4, SEQ ID NO:5, combinations thereof, or functional homolog thereof.

15. The method according to claim 9, wherein:
the at least one peptide sequence has a length ranging from 5 to 200 amino acids;
the at least one peptide sequence is located at the N-terminal and/or C-terminal relative to the polyesterase sequence; and
combinations thereof.

16. The method according to claim 9, wherein the at least one peptide sequence is covalently bonded to the polyesterase with a linker.

17. The method according to claim 9, wherein:
the peptide linker has a length ranging from 1 to 100 amino acids;
the peptide linker is selected from AEAAAKEAAAKEAAAKA (SEQ ID NO: 6), PPGG-NRGTTTTRRPATTTGSSPGP (SEQ ID NO:7), or homologs thereof; or combinations thereof.

18. The method according to claim 9, wherein the polyesterase has the following N-terminal to C-terminal orientation:
(i) polyesterase-SEQ ID NO:7-SEQ ID NO:2;
(ii) polyesterase-SEQ ID NO:7-SEQ ID NO:3;
(iii) polyesterase-SEQ ID NO:7-SEQ ID NO:4;
(iv) polyesterase-SEQ ID NO:7-SEQ ID NO:5;
(v) polyesterase-SEQ ID NO:6-SEQ ID NO:2;
(vi) polyesterase-SEQ ID NO:6-SEQ ID NO:3;
(vii) polyesterase-SEQ ID NO:6-SEQ ID NO:4; or
(viii) polyesterase-SEQ ID NO:6-SEQ ID NO:5.

19. The method according to claim 9, wherein the polyesterase comprises an amino acid sequence, which over its entire length, is at least 95% or more identical to the amino acid sequence given in SEQ ID: 1, SEQ ID NO: 11, or SEQ ID NO: 12.

* * * * *